(12) United States Patent
Kim

(10) Patent No.: US 12,290,318 B2
(45) Date of Patent: May 6, 2025

(54) DIGESTIVE ORGAN ENDOSCOPE SYSTEM

(71) Applicants: GACHON UNIVERSITY OF INDUSTRY-ACADEMIC COOPERATION FOUNDATION, Seongnam-si (KR); GIL MEDICAL CENTER, Incheon (KR)

(72) Inventor: Jung Ho Kim, Seoul (KR)

(73) Assignees: GACHON UNIVERSITY OF INDUSTRY-ACADEMIC COOPERATION FOUNDATION, Seongnam-si (KR); GIL MEDICAL CENTER, Incheon (KR)

( * ) Notice: Subject to any disclaimer, the term of this patent is extended or adjusted under 35 U.S.C. 154(b) by 941 days.

(21) Appl. No.: 16/962,219

(22) PCT Filed: Jan. 9, 2019

(86) PCT No.: PCT/KR2019/000359
§ 371 (c)(1),
(2) Date: Jan. 22, 2021

(87) PCT Pub. No.: WO2019/139356
PCT Pub. Date: Jul. 18, 2019

(65) Prior Publication Data
US 2021/0153952 A1    May 27, 2021

(30) Foreign Application Priority Data

Jan. 15, 2018 (KR) .................. 10-2018-0004847
Aug. 20, 2018 (KR) .................. 10-2018-0096782

(51) Int. Cl.
*A61B 34/20*    (2016.01)
*A61B 1/00*    (2006.01)
(Continued)

(52) U.S. Cl.
CPC .......... *A61B 34/20* (2016.02); *A61B 1/00055* (2013.01); *A61B 1/018* (2013.01);
(Continued)

(58) Field of Classification Search
CPC ............ A61B 1/00055; A61B 1/00133; A61B 1/00137; A61B 1/018; A61B 1/273;
(Continued)

(56) References Cited

U.S. PATENT DOCUMENTS

2003/0120150 A1    6/2003    Govari
2006/0130209 A1    6/2006    Golan
(Continued)

FOREIGN PATENT DOCUMENTS

JP    03-111025 A    5/1991
JP    10-248800 A    9/1998
(Continued)

OTHER PUBLICATIONS

International Search Report for PCT/KR2019/000359 mailed Apr. 18, 2019 from Korean Intellectual Property Office.

*Primary Examiner* — Michael T Rozanski
(74) *Attorney, Agent, or Firm* — Revolution IP, PLLC

(57) ABSTRACT

The present invention provides a digestive organ endoscope system which allows a user to perceive whether or not the tip of an endoscope instrument inserted along a channel approaches the tip of an endoscope channel portion within a certain distance, thereby being capable of quickly inserting the endoscope instrument up to a position close to the tip of the endoscope channel portion, and thus, it is possible to reduce a procedure time and to prevent a digestive organ from being damaged due to instantaneous protrusion of the tip of the endoscope instrument occurring when the endoscope instrument is quickly inserted.

2 Claims, 3 Drawing Sheets

(51) Int. Cl.
*A61B 1/018* (2006.01)
*A61B 1/273* (2006.01)
*A61B 5/06* (2006.01)

(52) U.S. Cl.
CPC .............. *A61B 1/273* (2013.01); *A61B 5/062* (2013.01); *A61B 2034/2051* (2016.02)

(58) Field of Classification Search
CPC ........... A61B 2017/00118; A61B 2017/00128; A61B 2017/00876; A61B 2034/2051; A61B 2090/0811; A61B 2090/374; A61B 2090/376; A61B 2090/3762; A61B 2090/378; A61B 2562/0257; A61B 34/20; A61B 5/062; A61B 90/361; A61B 90/37; A61B 90/98
See application file for complete search history.

(56) References Cited

U.S. PATENT DOCUMENTS

| | | |
|---|---|---|
| 2008/0188862 A1 | 8/2008 | Saitou |
| 2016/0183841 A1 | 6/2016 | Duindam et al. |
| 2017/0265723 A1* | 9/2017 | Yamaya .............. A61B 1/00096 |

FOREIGN PATENT DOCUMENTS

| | | |
|---|---|---|
| JP | 2003-019104 A | 1/2003 |
| JP | 2007-259998 A | 10/2007 |
| JP | 2012-016530 A | 1/2012 |
| JP | 5717991 B2 | 5/2015 |
| KR | 10-2003-0053039 A | 6/2003 |
| KR | 10-2006-0037253 A | 5/2006 |
| KR | 10-2012-0107267 A | 10/2012 |
| KR | 10-2016-0051738 A | 5/2016 |
| WO | 2017-163876 A1 | 9/2017 |

* cited by examiner

DIGESTIVE ORGAN ENDOSCOPE SYSTEM

CROSS REFERENCE TO PRIOR APPLICATIONS

This application is a National Stage Application of PCT International Patent Application No. PCT/KR2019/000359 filed on Jan. 9, 2019, under 35 U.S.C. § 371, which claims priority to Korean Patent Application Nos. 10-2018-0096782 filed on Aug. 20, 2018 and 10-2018-0004847 filed on Jan. 15, 2018, which are all hereby incorporated by reference in their entirety.

TECHNICAL FIELD

The present invention relates to an endoscope system, and more particularly, to a digestive organ endoscope system which allows a user to perceive using a sense (a tactile sense, an acoustic sense, or a visual sense) whether or not the tip of an endoscope instrument inserted along a channel of an endoscope approaches the tip of an endoscope channel, thereby being capable of quickly inserting the endoscope instrument to a vicinity of the tip of the endoscope channel without checking a position of the tip of the endoscope instrument one by one through a monitor while inserting the endoscope instrument.

BACKGROUND

A device for visually checking the inside of the human body includes various imaging devices such as an X-ray fluoroscope, an ultrasonic tester, and an NMR-CT.

The above-listed devices acquire information on abnormal parts of the human body by indirectly measuring the inside of the human body from the outside, or by combining or image-processing specific signals which are generated from the inside of the human body and received from the outside of the human body. The information acquired in this way is inadequate to acquire a clear image therefrom due to a distance to an imaging target, that is, the human body, or an error in a signal that is received and processed.

Therefore, in recent years, an endoscope instrument for acquiring an accurate image by directly inserting an imaging device into an abnormal part of the human body has been widely used.

A general digestive organ endoscope is a device for visually checking and diagnosing the inside of the human body, and the digestive organ endoscope can include a plurality of endoscope channels having a predetermined length, a camera arranged at the end of the endoscope channel, and an endoscope instrument (surgical tool) exposed through the tip of the endoscope channel.

A digestive organ endoscope of the related art is inserted into a digestive organ of a patient through an endoscope channel and can include an endoscope instrument (surgical tool) for observing or treating the inside of the digestive organ after being exposed from the tip of the endoscope channel.

As the endoscope instrument, any one of a tweezer, a scissor, and a forcep can be selectively used to operate or incise an affected area, and in addition, a hook, a scalpel, a pin, and an electrocautery (an instrument that performs incision or hemostasis by burning tissue with heat generated by a high electric current flowing through a local area of the human body) can also be selectively used.

There is a problem in that an endoscope instrument can unintentionally come into contact with an inner wall of an digestive organ to cause a wound on the inner wall when the endoscope instrument comes out of the tip of an endoscope channel to observe or treat the inside of the digestive organ.

In order to solve the above problem, Korea Patent Publication No. 10-2012-0107267 (2012 Oct. 2) was provided as a technique of the related art.

However, in order to check whether or not an inserted endoscope instrument reaches the tip (end) of an endoscope, whether or not the tip of the endoscope instrument protrudes from the channel is checked through a screen, and when the tip of the endoscope instrument protrudes, it is determined that the endoscope instrument reaches the tip of the endoscope, and if the endoscope instrument is pushed in quickly, the endoscope instrument may damage the stomach of a patient through the tip of the endoscope channel, and accordingly, in order to reduce the damage, the endoscope instrument has to be slowly pushed until it is visible on the screen, and thereby, much time is spent on the insertion of the endoscope instrument.

SUMMARY OF INVENTION

Technical Problem

The present invention aims to provide a digestive organ endoscope system which allows a user to perceive whether or not the tip of an endoscope instrument inserted along a channel approaches the tip of an endoscope channel portion within a certain distance, thereby being capable of quickly inserting the endoscope instrument up to a position close to the tip of the endoscope channel portion, and thus, It is possible to reduce a procedure time and to prevent a digestive organ from being damaged due to instantaneous protrusion of the tip of the endoscope instrument occurring when the endoscope instrument is quickly inserted.

Solution to Problem

A digestive organ endoscope system according to the present invention includes an endoscope instrument that is inserted into a digestive organ of a patient and observes or treats an inside of the digestive organ; an endoscope channel portion in which a channel through which the endoscope instrument moves is formed; and a sensing portion that informs a user whether or not a tip of the endoscope instrument approaches a tip of the endoscope channel portion at a set distance or less.

The sensing portion may be formed to protrude outward in a periphery of the endoscope instrument and may include a protrusion member that comes into contact with an inlet of the endoscope channel portion when the tip of the endoscope instrument approaches the tip of the endoscope channel portion at a set distance or less.

The protrusion member may be formed of a silicone material and may be formed as a ring having a space into which the endoscope instrument is inserted in the center.

The protrusion member may be a coating layer formed on an outer circumference of the endoscope instrument, and the coating layer may be formed of silicone or a Teflon material.

The protrusion member may be formed of a plurality of protrusions spaced apart from each other in a longitudinal direction of the endoscope instrument.

The present invention may further include a packing member that is formed in an inlet of the channel, has a diameter equal to an outer diameter of the endoscope instrument, and has an insertion hole into which the endoscope instrument is inserted, and the packing member may be formed of a rubber material.

An inner diameter of the inlet of the channel may be equal to the outer diameter of the endoscope instrument, and the sensing portion may be formed as a groove formed in a periphery of the endoscope instrument.

The sensing portion may include a tag that is formed in the endoscope instrument and generates magnetism, and detection means that is formed in the endoscope channel portion and informs a user whether or not the tip of the endoscope instrument approaches a tip of a channel of the endoscope channel portion at a set distance or less by detecting the magnetism generated by the tag.

The sensing portion may include a tag that is formed in the endoscope instrument and transmits an electronic signal (RF signal), and detection means that is formed in the endoscope channel portion and informs a user whether or not the tip of the endoscope instrument approaches a tip of a channel of the endoscope channel portion at a set distance or less by detecting the electronic signal generated by the tag, and the detection means may generate an alarm sound when the tip of the endoscope instrument is determined to approach the tip of the endoscope channel portion at a set distance or less.

Advantageous Effects

A digestive organ endoscope system of the present invention has the following effects.

First, when the tip of an endoscope instrument inserted along a channel of an endoscope channel portion approaches the tip of the endoscope channel portion within a certain distance, a user can immediately perceive the approaching with the sense (a tactile sense, an acoustic sense, or a visual sense), thereby being capable of quickly inserting the endoscope instrument up to a position close to the tip of the endoscope channel portion, and thus, there is an effect of significantly reducing a procedure time.

Second, there is an effect of preventing the digestive organ from being damaged due to an instantaneous protrusion of the tip of the endoscope instrument occurring when the endoscope instrument is quickly inserted.

BEST MODE FOR INVENTION

Figure 1:
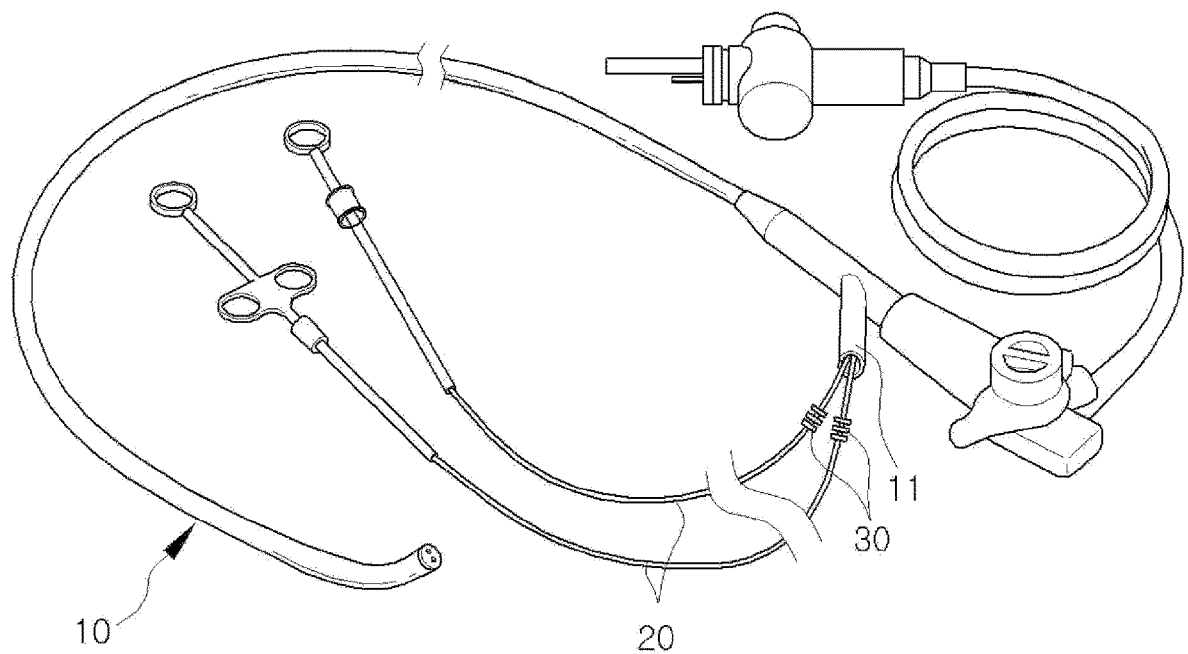
FIG. 1 is a perspective view of a digestive organ endoscope system according to a first embodiment of the present invention.

The present invention includes an endoscope instrument that is inserted into a digestive organ of a patient and observes or treats an inside of the digestive organ; an endoscope channel portion in which a channel through which the endoscope instrument moves is formed; and a sensing portion that informs a user whether or not a tip of the endoscope instrument approaches a tip of the endoscope channel portion at a set distance or less, thereby being capable of quickly inserting the endoscope instrument up to a position close to the tip of the endoscope channel portion, and thus, it is possible to reduce a procedure time and to prevent a digestive organ from being damaged due to instantaneous protrusion of the tip of the endoscope instrument occurring when the endoscope instrument is quickly inserted.

DETAILED DESCRIPTION OF INVENTION

Hereinafter, preferred embodiments of the present invention will be described in detail with reference to the accompanying drawings. Prior to this, terms or words used in the present specification and claims should not be construed as being limited to usual meaning or dictionary meaning, and should be construed as meaning and concept consistent with the technical idea of the present invention, based on the principle that concept of the terms can be appropriately defined in order for the inventor to explain his/her own invention in the best way.

Therefore, the embodiments described in the present specification and the configurations illustrated in the drawings are only the most preferred embodiments of the present invention, and do not represent all of the technical idea of the present invention, and thus, it should be understood that there may be replaceable equivalent modification examples at the time of the present application.

The present invention relates to a digestive organ endoscope system which allows a user to perceive using a sense (a tactile sense, an acoustic sense, or a visual sense) whether or not the tip of an endoscope instrument inserted along a channel of an endoscope reaches a position close to the tip of an endoscope channel, thereby being capable of quickly inserting the endoscope instrument up to the position close to the tip of the endoscope channel without checking a position of the tip of the endoscope instrument one by one through a monitor while inserting the endoscope instrument.

Figure 2:
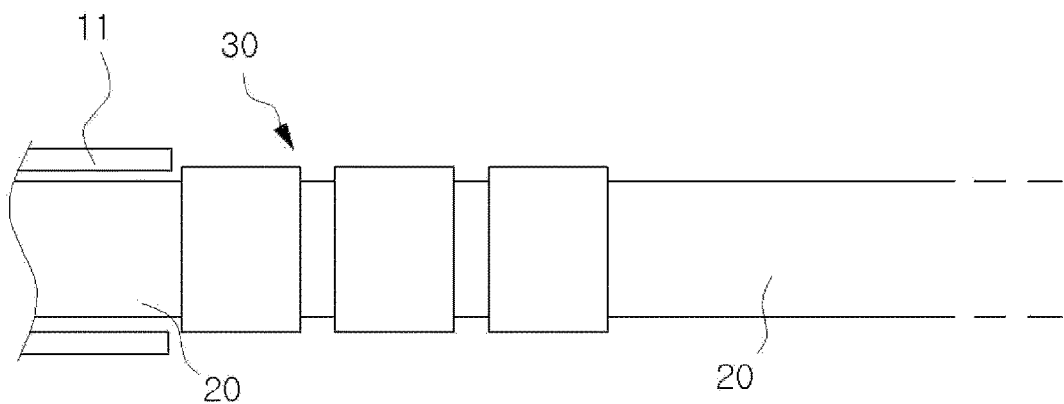
FIG. 2 is a side view of a sensing portion of the digestive organ endoscope system of FIG. 1.

Referring to FIGS. 1 and 2, a digestive organ endoscope system according to a first embodiment of the present invention includes an endoscope channel portion 10 and endoscope instruments 20. The endoscope channel portion 10 has a plurality of channels 11, each having a hollow formed therein and having a camera arranged at the tip of any one of the plurality of channels 11. The tip of the endoscope channel 10 can be inserted into the digestive organ through the mouth or anus of the digestive organ to observe the inside of the digestive organ.

In addition, the endoscope instruments 20 are inserted along the channels 11 of the endoscope channel portion 10 from the rear of the endoscope channel portion 10 to be exposed to the tip of the endoscope channel portion 10 such that the tip of the endoscope channel portion 10 performs a function thereof, and here, the endoscope instruments 20 may include various instruments such as a snare, an injector, and a forcep which are used for an endoscopic procedure. An inner diameter of an inlet of a channel of the endoscope channel portion is formed to be equal to or larger than an outer diameter of the endoscope instrument such that the endoscope instrument can be introduced into the channel 11.

At this time, sensing portions 30 are formed on rear sides of the endoscope instruments 20.

Each of the sensing portions 30 can be formed as protrusion members protruding outward from a periphery of the rear side of each of the endoscope instruments 20 so as to inform a user whether or not the tip of the endoscope instrument approaches the tip of the endoscope channel portion at a set distance or less. The set distance is a distance between the tip of the endoscope instrument and the tip of the endoscope channel portion when the tip of the endoscope instrument approaches the tip of the endoscope channel portion and is determined by a user in consideration of safety, and the protrusion members are arranged in consideration of the distance.

The protrusion members are formed at the rear of the endoscope instrument to come into contact with the inlet of the channel of the endoscope channel portion, when the tip of the endoscope instrument reaches the set distance from the tip of the endoscope channel portion while the endoscope instrument is inserted into the endoscope channel portion. It is formed in the rear. The protrusion members are formed to protrude outward more than an inner surface of the inlet of the endoscope channel portion such that a user can feel frictional resistance when the protrusion members pass through the inlet of the endoscope channel portion. The user perceives that the tip of the endoscope instrument reaches the set distance from the tip of the endoscope channel portion according to the resistance and slowly advances the endoscope instrument thereafter. Accordingly, an insertion time of the endoscope instrument can be reduced, and thereby, a procedure time is reduced.

In addition, in the present embodiment, each of the sensing portions 30 is described as protrusion members protruding outward from each of the endoscope instruments 20 itself but is not limited thereto and can be formed as a ring shaped member having a space into which the endoscope instrument is inserted in the center thereof.

The ring-shaped sensing portion 30 is preferably formed of a silicone material that is harmless to the human body and has elasticity. In this case, there is an advantage in that the endoscope instrument 20 can selectively adjust a position of the sensing portion 30 and can be more conveniently applied to the endoscope instrument 20 of the related art to which the sensing portion 30 is not applied.

Meanwhile, the sensing portion can also be formed as a coating layer formed on an outer circumference of the endoscope instrument. The coating layer can be formed to protrude outward from the outer circumference of the endoscope instrument and can be formed of silicone or a Teflon material.

In addition, protrusions, which are the sensing portion 30 according to the first embodiment of the present invention, are described to be limited to being formed as protruding nodes, but the present invention is not limited thereto, and the protrusions which are the sensing portion 30 can also be formed as dot-shaped points.

In addition, a plurality of the sensing portions 30 can be formed at equal intervals in a longitudinal direction from the rear side of the endoscope instrument 20 to the tip thereof such that a reaching distance to the tip of the endoscope channel 11 can be perceived step by step.

For example, protrusions, which are the sensing portion 30, can be formed at intervals of 5 cm in the rear end of the endoscope instrument 20 toward the tip thereof, and while the endoscope instrument 20 is inserted into the endoscope channel 11, a user can perceive the sensing portion 30 of the endoscope instrument 20, thereby, guessing a position of the tip of the endoscope instrument 20 inserted along the endoscope channel 11, and through this, the degree of approach to the tip of the endoscope channel 11 can be predicted.

Meanwhile, a user can also perceive that the tip of the endoscope instrument approaches the tip of the endoscope channel portion by a tactile sensation of a finger of the user.

While the endoscope instrument 20 is inserted into the channel 11 of the endoscope channel portion 10, when the endoscope instrument 20 reaches the vicinity of the tip of the channel 11, the protrusion members provide a protruding touch to the finger of the user such that the user can perceive that the tip of the endoscope instrument 20 reaches the vicinity of the tip of the channel 11 by a tactile sensation of a finger.

At this time, the protrusion members, which are the sensing portion 30, are composed of a plurality of protrusions formed to be spaced apart from each other in a longitudinal direction of the endoscope instrument, and the number of protrusions can be increased or decreased in inverse proportion to a reaching distance, and a user can count the reaching distance to the tip of the endoscope channel 11 with the number of protruding nodes delivered through a finger.

Meanwhile, at the inlet of the channel of the endoscope channel portion, an insertion hole into which the endoscope instrument is inserted can be formed in the center thereof, and a packing member coupled to the endoscope channel portion can be formed. The insertion hole of the packing member is formed to have the same diameter as an outer diameter of the endoscope instrument and is formed of a rubber material.

When the protrusion members of the endoscope instrument pass through the insertion hole, the packing member comes into contact with the protrusion members and generates frictional resistance, thereby, informing a user that the tip of the endoscope instrument approaches the tip of the endoscope channel portion.

Figure 3:
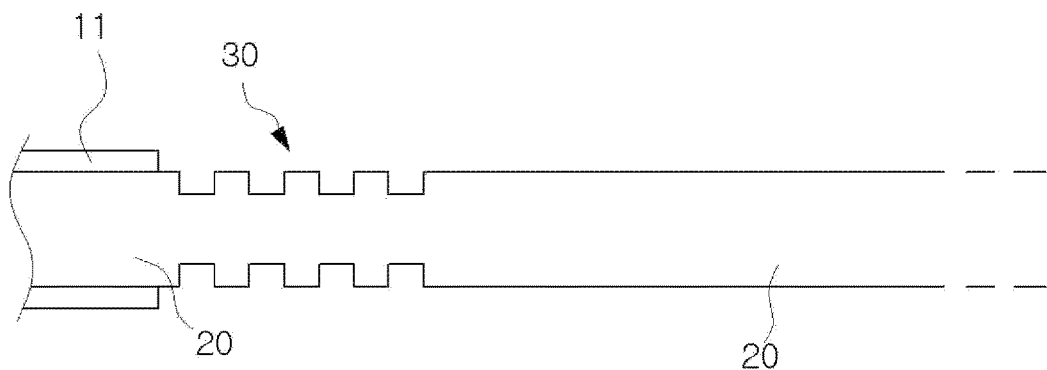
FIG. 3 is a side view of a sensing portion of a digestive organ endoscope system according to a second embodiment of the present invention.

Referring to FIG. 3, the sensing portion 30 of the digestive organ endoscope system according to a second embodiment of the present invention is formed of grooves formed around the endoscope instrument.

An outer diameter of the endoscope instrument is formed to be equal to an inner diameter of an inlet of the endoscope channel portion, and the endoscope instrument advances to the channel while generating a certain frictional resistance.

When the tip of the endoscope instrument reaches a set distance from the tip of the endoscope channel portion, the sensing portion passes through the inlet of the channel of the endoscope channel portion. When the sensing portion formed as concave grooves passes through the inlet of the endoscope channel portion, a frictional resistance between the endoscope instrument and the inlet of the endoscope channel portion is rapidly reduced, and thus, a user can perceive that the tip of the endoscope instrument reaches the set distance from the tip of the endoscope channel portion.

Thereafter, the user slowly advances the endoscope instrument, and thereby, the endoscope instrument safely protrudes from the tip of the endoscope channel portion.

Meanwhile, in the sensing portion formed as concave grooves inwardly engraved in the periphery of the endoscope instrument 20, the grooves provide groove (sink) feel to a user's finger when the grooves reach the vicinity of the tip of the channel 11 while the endoscope instrument 20 is inserted into the channel 11 of the endoscope 10, and thereby, the user can also perceive that the endoscope instrument 20 reaches the vicinity of the tip of the channel 11 by a tactile sensation of a finger of the user.

Here, the grooves can be formed as engraved groove nodes along an outer circumference of any one point on the rear side of the endoscope instrument 20 to provide the groove feel to the finger of the user.

In addition, a plurality of the sensing portions 30 can be formed at equal intervals in a longitudinal direction from the rear side of the endoscope instrument 20 such that a reaching distance to the tip of the endoscope channel 11 can be perceived step by step.

For example, the grooves, which are the sensing portion 30, can be formed at intervals of 5 cm in the rear end of the endoscope instrument 20 toward the tip thereof, and while the endoscope instrument 20 is inserted into the endoscope channel 11, a user can perceive the sensing portion 30 of the endoscope instrument 20 by a tactile sensation delivered through a finger, thereby, guessing a position of the tip of the endoscope instrument 20 inserted along the endoscope channel 11, and through this, a reaching distance of the tip of the endoscope instrument 20 to the tip of the endoscope channel 11 can be calculated.

At this time, the number of the groove nodes, which are the sensing portion 30, can be increased or decreased in inverse proportion to the reaching distance, and a user can calculate the reaching distance to the tip of the endoscope channel 11 with the number of groove nodes delivered through a finger of the user.

In addition, the sensing portions 30 may be formed by gradually reducing intervals therebetween in inverse proportion to the reaching distance. For example, each of the sensing portions 30 can also be formed on an outer circumferential surface of the endoscope instrument corresponding to the inlet of the channel of the endoscope channel portion, when the tip of the endoscope instrument 20 reaches 50 cm, 30 cm, 10 cm, 5 cm, and 4 cm before the tip of the endoscope channel 11.

Figure 4:
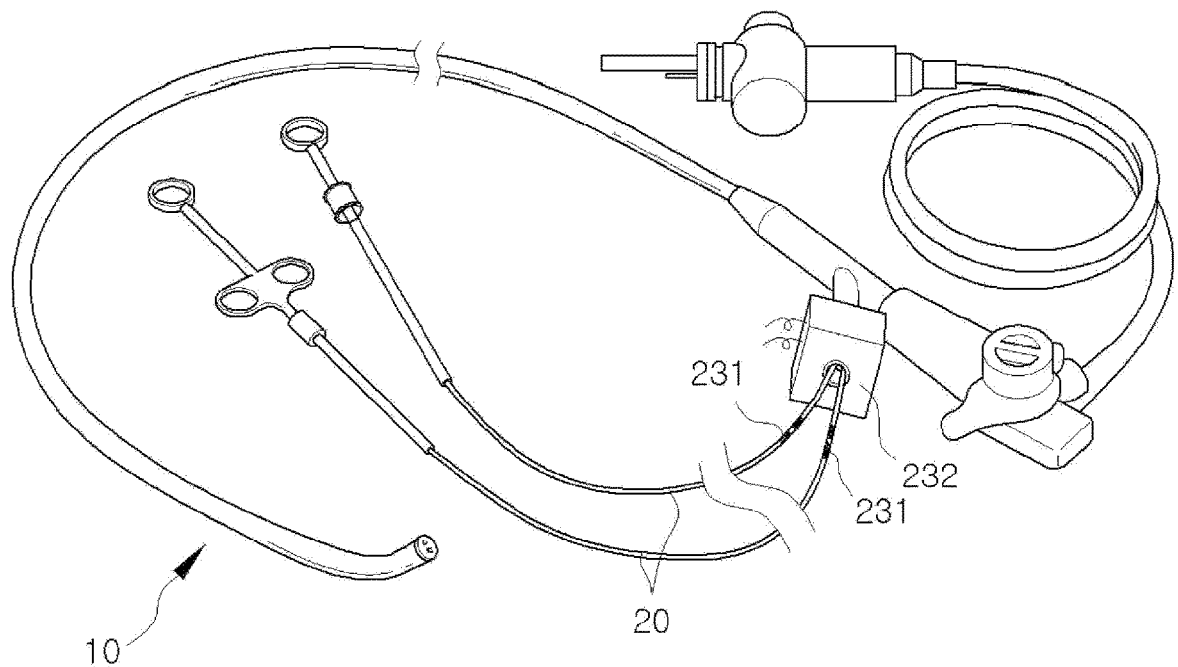
FIG. 4 is a perspective view of a digestive organ endoscope system according to a third embodiment of the present invention.
Figure 5:
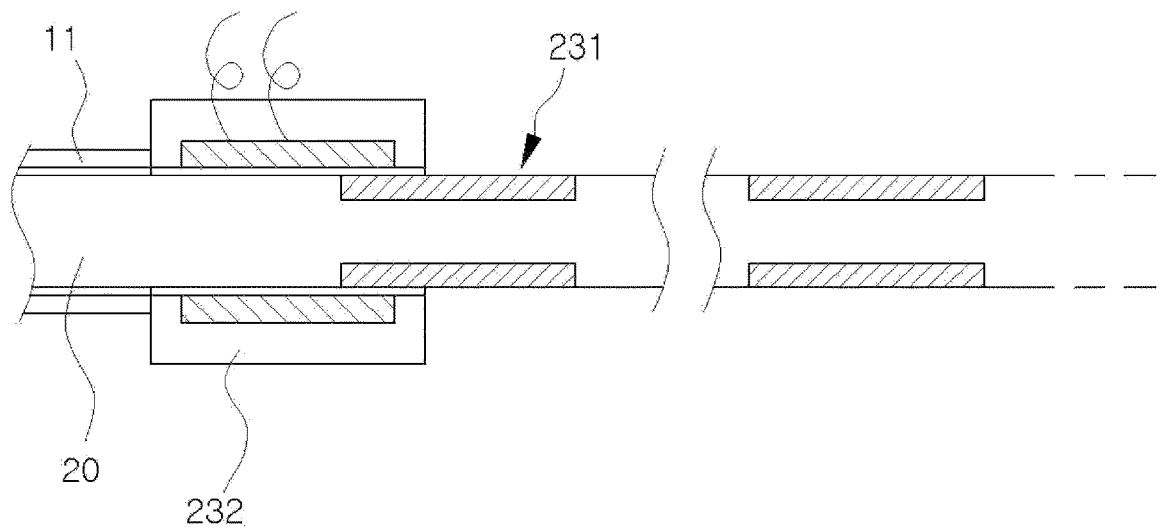
FIG. 5 is a cross-sectional view of a sensing portion of the digestive organ endoscope system according to the third embodiment of the present invention.

Referring to FIGS. 4 and 5, a sensing portion of a digestive organ endoscope system according to a third embodiment of the present invention includes tags and detection means.

The tag 231 is formed at the rear of an endoscope instrument and generates magnetism. The tag is inwardly buried in a periphery of the endoscope instrument 20 inserted into the channel 11 of the endoscope channel. When the tip of the endoscope instrument reaches a set distance from the tip of an endoscope channel portion, the tag 231 passes through one side of the detection means 232. The detection means detects magnetism generated by the tag.

When the magnetism generated by the tag is detected, a control portion electrically connected to the detection means 232 generates sound (alarm sound) and vibration to inform a user who inserts the endoscope instrument 20 into the channel 11 of the endoscope channel portion 10 that the tip of the endoscope instrument approaches the tip of the endoscope channel portion. Accordingly, the user can know whether or not the tip of the endoscope instrument approaches the tip of the endoscope channel portion at a set distance or less.

In addition, a plurality of the tags 231 are formed at equal intervals in a longitudinal direction from a rear side of the endoscope instrument 20 to the tip side thereof such that a distance between the tip of the endoscope instrument and the tip of the endoscope channel 11 can be perceived step by step.

For example, a plurality of magnetic tags 231 can be formed at predetermined intervals from the rear of the endoscope instrument 20 toward the tip thereof. When a user inserts the endoscope instrument 20 into the endoscope channel 11, the detection means 232 detects magnetism generated by the tag 231 and allows the user to perceive the magnetism, and thereby, a position of the tip of the endoscope instrument 20 inserted into the channel 11 can be guessed, and through this, a distance between the tip of the endoscope instrument 20 and the tip of the endoscope channel 11 can be calculated.

Each of the tags can be formed at a position corresponding to an inlet of the channel of the endoscope channel portion, when the tip of the endoscope instrument 20 is at positions of 50 cm, 30 cm, 10 cm, 5 cm, and 4 cm before reaching the tip of the endoscope channel 11.

Therefore, in a case where the endoscope instrument 20 is inserted into the channel 11, the tag 231 which is formed on the rear side of the endoscope instrument 20 and informs that the tag is placed at a position of 50 cm before reaching the tip of the endoscope channel 11 passes through the detection means 232, the detection means 40 detects the tag 231 placed at the position of 50 cm before reaching the tip of the endoscope channel 11, and a sound corresponding to the reaching distance is output through the control portion to inform a user who inserts the endoscope instrument 20 into the endoscope channel 11 that the tip of the endoscope instrument approaches the tip of the endoscope channel portion at 50 cm or less.

In addition, when the endoscope instrument 20 is continuously inserted to reach a position of 30 cm before the tip of the endoscope instrument 20 reaches the tip of the endoscope channel 11, the detection means detects the tag placed at the position of 30 cm before reaching the tip of the channel 11 and generates a sound corresponding to the reaching distance. Accordingly, a user can calculate a distance between the tip of the endoscope and the tip of the endoscope channel portion.

In addition, the tag which is the sensing portion 30 and transmits magnetism can also be formed as a protruding node protruding outward from the periphery of the endoscope instrument 20. In this case, as in the first embodiment of the present invention, whether or not the tip of the endoscope instrument 20 reaches a distance close to the tip of the endoscope channel 11 can be checked through a change in frictional resistance due to the protruding node.

In addition, not only a signal detected by the detection means 40 is output as a sound through a control portion, but also a remaining distance before the tip of the endoscope instrument 20 reaches the tip of the endoscope channel 11 is displayed on a screen of a monitor connected to the endoscope such that a user can also perceive intuitively a reach distance of the endoscope instrument 20.

Figure 6:
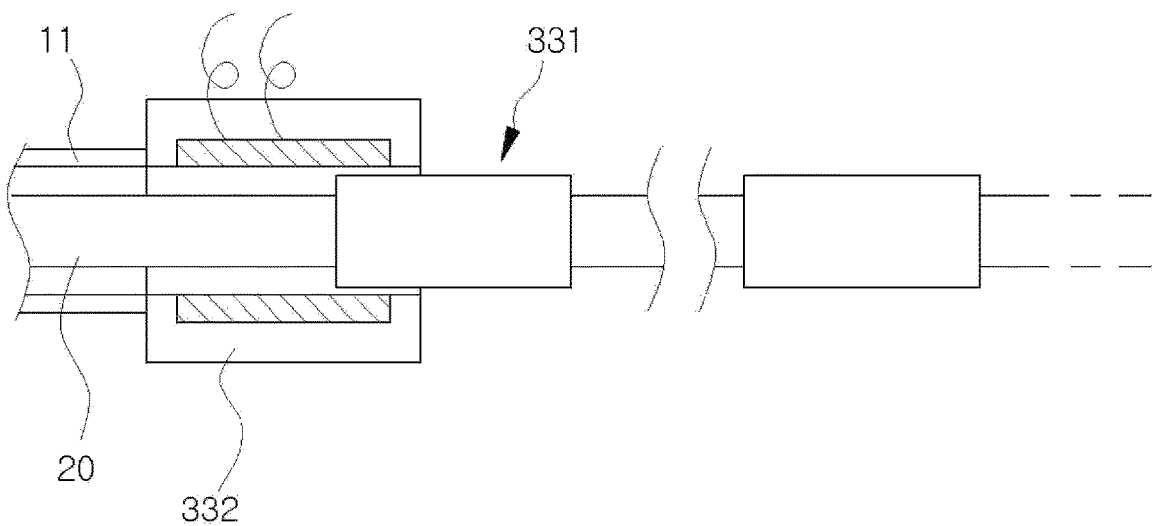
FIG. 6 is a cross-sectional view of a sensing portion of a digestive organ endoscope system according to a fourth embodiment of the present invention.

Referring to FIG. 6, a sensing portion of a digestive organ endoscope system according to a fourth embodiment of the present invention includes tags that generate an electronic signal and detection means.

The tag is mounted on a rear end of the endoscope instrument and transmits an electronic signal (RF signal). In addition, detection means 40, which senses the tag 331 provided on the rear end side of the endoscope instrument 20 and generate a signal corresponding thereto, is included in the rear end of the channel 11 of the endoscope channel portion 10.

When the tip of the endoscope instrument reaches a set distance from the tip of the endoscope channel portion, the tag 331 passes through one side of the detection means 332. The detection means detects an electronic signal generated from the tag and outputs a signal that can be perceived by a user through an acoustic sense and a tactile sense after detecting the electronic signal.

In addition, the output signal is expressed as a sound (alarm sound) and vibration by a control portion electrically connected to the detection means 332 and is perceived by a user who inserts the endoscope instrument 20 into the channel 11 of the endoscope channel portion 10. Accordingly, the user can know whether or not the tip of the endoscope instrument approaches the tip of the endoscope channel portion at a set distance or less.

In addition, a plurality of the tags 331 are formed at equal intervals in a longitudinal direction from the rear side of the endoscope instrument 20 to the tip side thereof such that a distance between the tip of the endoscope instrument 20 and the tip of the channel 11 I can be perceived step by step.

The present invention is described with reference to the embodiments illustrated in the drawings, but the embodiments are merely examples, and those skilled in the art will appreciate that various modifications and equivalent other embodiments are possible therefrom. Accordingly, the true technical protection scope of the present invention should be determined by the technical idea of the appended claims.

The invention claimed is:

1. A digestive organ endoscope system comprising:
    an endoscope instrument that is configured to be inserted into a digestive organ of a patient and observes or treats an inside of the digestive organ;
    an endoscope channel portion in which a channel through which the endoscope instrument moves is formed; and
    a sensing portion that informs a user whether or not a tip of the endoscope instrument approaches a tip of the endoscope channel portion at a set distance or less,
    wherein the sensing portion includes a plurality of tags that generate magnetism, wherein each of the plurality of tags is formed at a position corresponding to an inlet of the channel of the endoscope channel portion when the tip of the endoscope instrument is at positions of a first predetermined distance, a second predetermined distance, a third predetermined distance, a fourth predetermined distance, and a fifth predetermined distance before reaching the tip of the endoscope channel,
    wherein the plurality of tags are formed by gradually reducing intervals therebetween in inverse proportion to a reaching distance,
    wherein a detector generates an alarm sound corresponding to the reaching distance as the tip of the endoscope instrument approaches to the tip of the endoscope channel portion at a set distance.

2. A digestive organ endoscope system comprising:
    an endoscope instrument that is configured to be inserted into a digestive organ of a patient and observes or treats an inside of the digestive organ;
    an endoscope channel portion in which a channel through which the endoscope instrument moves is formed; and
    a sensing portion that informs a user whether or not a tip of the endoscope instrument approaches a tip of the endoscope channel portion at a set distance or less,
    wherein the sensing portion includes a plurality of tags that transmit an electronic signal which is RF signal, wherein each of the plurality of tags is formed at a position corresponding to an inlet of the channel of the endoscope channel portion when the tip of the endoscope instrument is at positions of a first predetermined distance, a second predetermined distance, a third predetermined distance, a fourth predetermined distance, and a fifth predetermined distance before reaching the tip of the endoscope channel,
    wherein the plurality of tags are formed by gradually reducing intervals therebetween in inverse proportion to a reaching distance,
    wherein a detector generates an alarm sound corresponding to the reaching distance as the tip of the endoscope instrument approaches to the tip of the endoscope channel portion at a set distance.

* * * * *